(12) United States Patent
Griffith et al.

(10) Patent No.: US 9,176,050 B2
(45) Date of Patent: Nov. 3, 2015

(54) METHOD AND APPARATUS FOR INCREASED PURGE EFFICACY IN OPTICAL ABSORPTION SPECTROSCOPIC MEASUREMENTS OF GASES IN SEALED CONTAINERS

(71) Applicant: LIGHTHOUSE INSTRUMENTS, LLC., Charlottesville, VA (US)

(72) Inventors: Warren M. Griffith, Charlottesville, VA (US); William R. Anderson, Charlottesville, VA (US); Peter J. Leavesley, Charlottesville, VA (US); Michael A. Timmins, Charlottesville, VA (US)

(73) Assignee: LIGHTHOUSE INSTRUMENTS, LLC., Charlottesville, VA (US)

( * ) Notice: Subject to any disclaimer, the term of this patent is extended or adjusted under 35 U.S.C. 154(b) by 0 days.

(21) Appl. No.: 13/839,774

(22) Filed: Mar. 15, 2013

(65) Prior Publication Data
US 2013/0293892 A1 Nov. 7, 2013

Related U.S. Application Data

(60) Provisional application No. 61/642,213, filed on May 3, 2012.

(51) Int. Cl.
*G01N 21/00* (2006.01)
*G01N 21/27* (2006.01)
*G01N 21/15* (2006.01)
*G01N 21/31* (2006.01)

(52) U.S. Cl.
CPC ............... *G01N 21/27* (2013.01); *G01N 21/15* (2013.01); *G01N 21/31* (2013.01); *G01N 2021/151* (2013.01)

(58) Field of Classification Search
CPC ............ G01N 21/3504; G01N 21/359; G01N 33/4925; G01N 2021/052; G01N 2021/396; G01N 21/031; G01N 21/27; G01N 21/31; G01N 21/3518; G01N 21/37; G01N 21/61; G01N 2201/0221; G01N 2201/1215; G01N 33/00
USPC .................. 356/437–440, 432; 73/866.5; 250/223 B, 343; 436/47
See application file for complete search history.

(56) References Cited

U.S. PATENT DOCUMENTS

| | | | |
|---|---|---|---|
| 5,340,987 A * | 8/1994 | Eckles et al. | 250/345 |
| 5,482,842 A | 1/1996 | Berndt | |
| 6,639,678 B1 | 10/2003 | Veale et al. | |
| 7,067,323 B2 | 6/2006 | Veale et al. | |

* cited by examiner

*Primary Examiner* — Tri T Ton
(74) *Attorney, Agent, or Firm* — Greenblum & Bernstein, P.L.C.

(57) ABSTRACT

A system and method for nondestructive detection of gas in a sealed container. The system includes a light source housed in a light source housing and configured to emit a light beam for absorption in a substance to be measured, a detector housed in a detector housing and configured to detect the emitted light beam, a zone that accepts one or more of the sealed containers, each container being substantially optically transparent and containing the substance to be measured, the zone located between the detector and the light source, the light source configured to transmit the light beam through the zone, and a light source purging system comprising a light source channel surrounding the light source and positioned between the light source and the housing, the light source channel configured to expel purge gas from a purge gas source into the zone.

26 Claims, 5 Drawing Sheets

METHOD AND APPARATUS FOR INCREASED PURGE EFFICACY IN OPTICAL ABSORPTION SPECTROSCOPIC MEASUREMENTS OF GASES IN SEALED CONTAINERS

CROSS-REFERENCE TO RELATED APPLICATIONS

The instant application claims the benefit of priority of U.S. provisional application No. 61/642,213, filed May 3, 2012, the disclosure of which is herein expressly incorporated by reference in its entirety.

BACKGROUND

1. Field of the Disclosure

The present disclosure relates to the field of optical absorption laser spectroscopy. More particularly, the present disclosure relates to a method and apparatus for increased purge efficacy in optical absorption spectroscopic measurements of gases in sealed containers.

2. Background Information

There presently exist systems in which gases in volume product containers are detected, analyzed and/or measured during pharmaceutical, food and beverage, consumer electronic production and the like. Optical absorption laser spectroscopy can quantify the amount of matter in a sample by directing laser energy at a sample of matter and measuring how much laser intensity is absorbed. Such systems can measure trace quantities and can nondestructively analyze gas contents within sealed containers, in order to determine, e.g., the amount of contaminants/species present in a sealed container.

Figure 1:
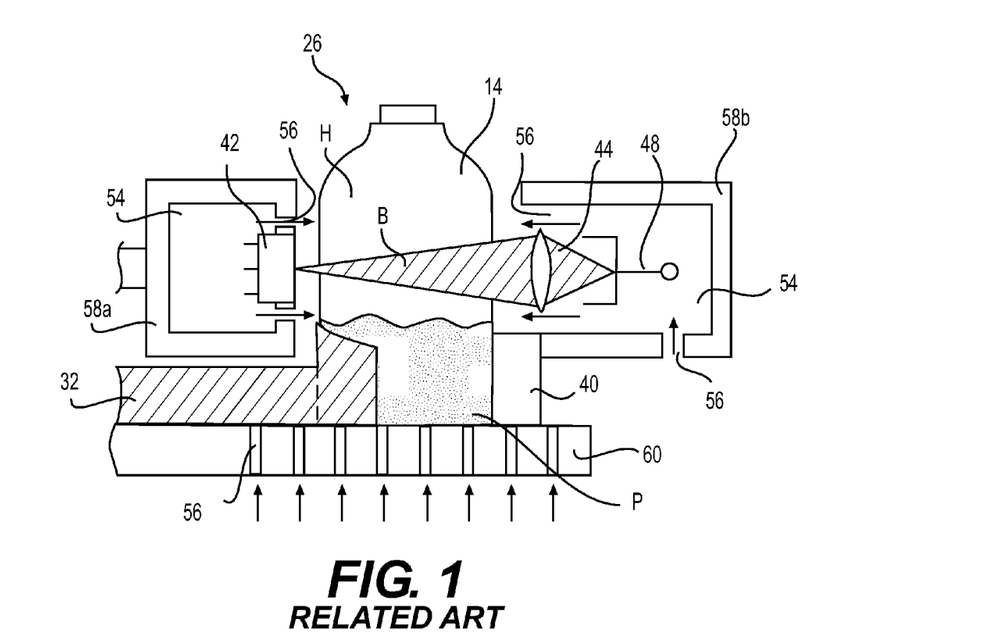
FIG. 1 shows a schematic side sectional view of a related art optical absorption laser spectroscopy system.

FIG. 1 shows a related art optical absorption laser spectroscopy system 10 found in, e.g., U.S. Pat. No. 7,067,323, the contents of which are expressly incorporated herein in their entirety. Such a system 10 generally contains a light source 42, a container 14, a light collection element 44, and a light detector 48, and can be an enclosed design.

The region between the light source 42 and the light detector 48 is typically referred to as a sample region or detection zone 26. In other words, in the detection zone 26, the light emitted from the light source 42 passes through the detection zone along the optical axis of the light source and onto the detector. The light is of a special variety that is absorbed by a spectroscopic species of interest in a way that is detectable, which is considered the signal to be detected. The light collection is usually done with an optical lens 44. The optical path B includes the light rays that are emitted by the laser light source 42 and also sensed by the detector 48. Absorbers that are outside of the container 14 yet within the optical path B can adversely affect the signal picked up by the detector 48 as well as absorbers that are inside. To reduce or eliminate the effect of these external absorbers, some other inert gas (that does not contain absorbers, such as nitrogen) can be pumped into the optical path B from a gas source by a purging system 54 to displace or remove the ambient gas from the top of the detection zone 26, which is referred to as a purge. By purging the unwanted gas or air through passages 56, the system 10 can better determine solely the concentration of absorbers within a container, and to a high degree of accuracy.

For example, when detecting oxygen in a sealed pharmaceutical sample container, the oxygen in the atmosphere outside the container but along the laser path must be removed. Purging this gas away from the sample container is often the quickest and most efficient method for removing interfering gas species from the measurement region.

Optical absorption laser spectroscopy using sealed containers 14 that move quickly through the detection zone 26 can be a challenge due to the entrained flow of such as ambient air. A closed system where a purge gas can reliably displace all ambient gas and where the container to be measured is inserted into the apparatus can be forgiving with respect to the particular flow of the purge, so long as it is good enough to remove most of the ambient gas eventually, as the physical limitations of it are such that measurements take tens of seconds to minutes.

Figure 2:
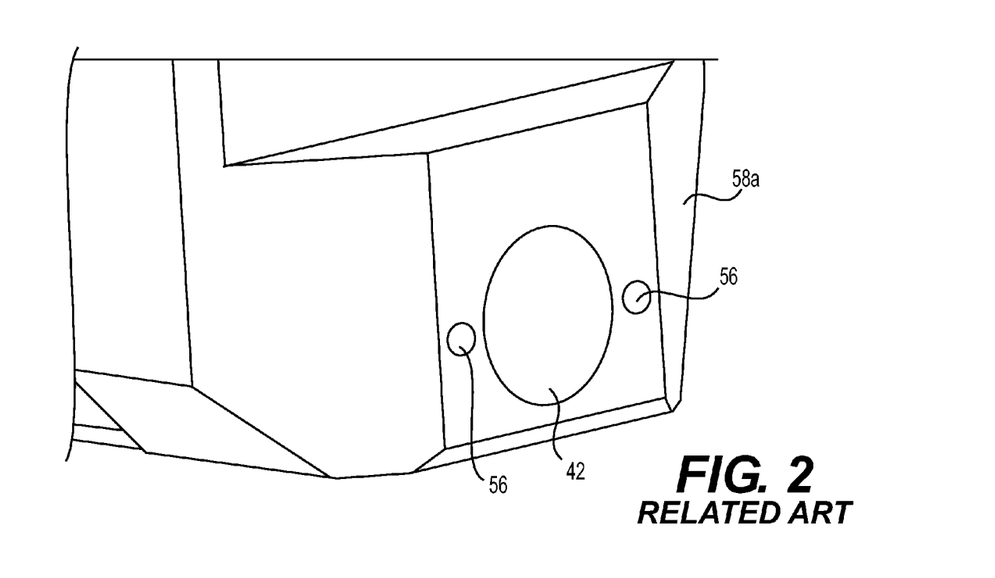
FIG. 2 shows a schematic perspective view of a related art laser source.
Figure 3:
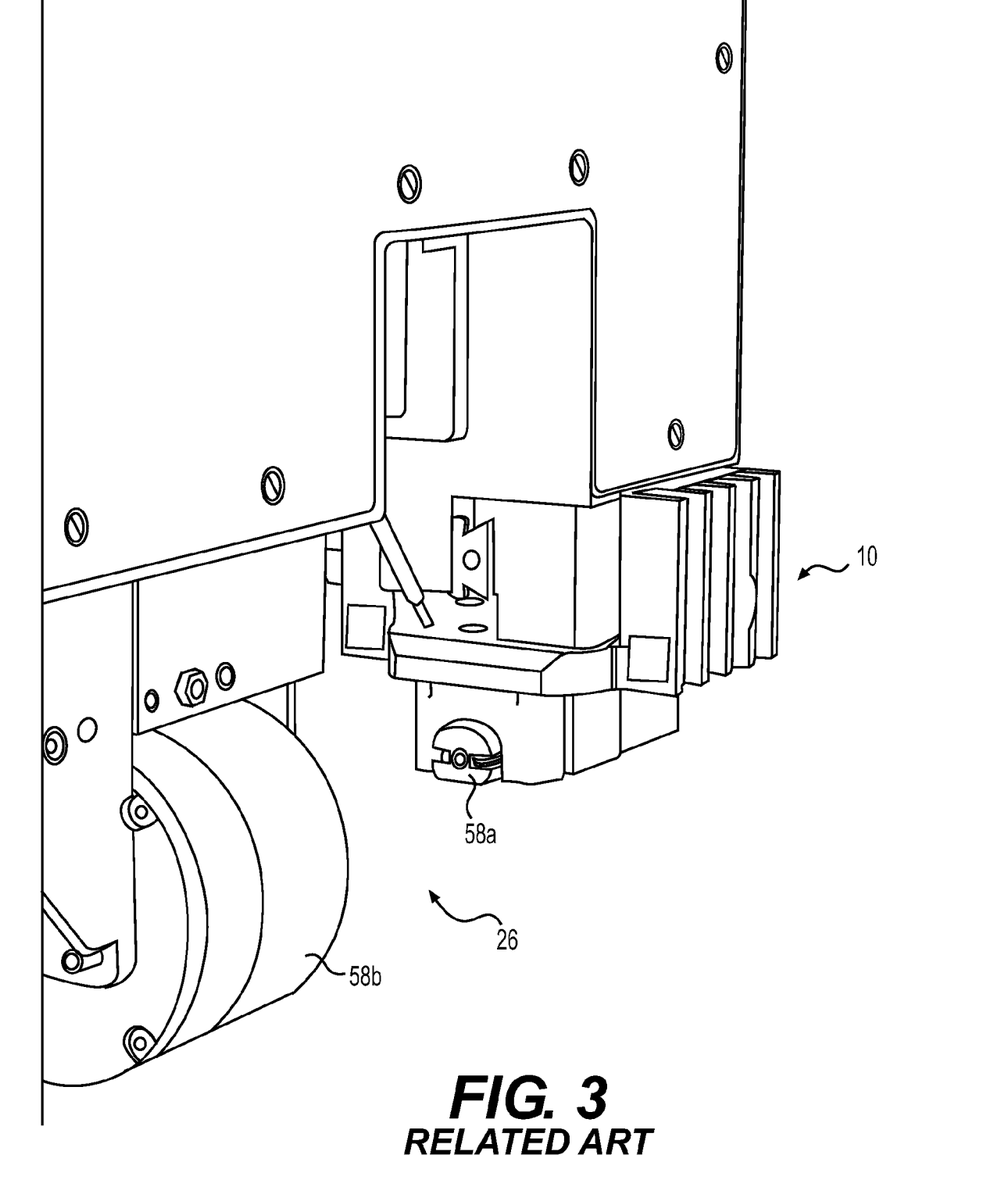
FIG. 3 shows a perspective view of the related art optical absorption laser spectroscopy system.

FIG. 2 shows a laser module of a related art optical absorption laser spectroscopy system. In this example, the laser source 42 is present in laser source housing 58a, and includes a pair of passages 56 in the form of purge holes on opposite sides of the laser source. The flow of purge gas must be high in order to discharge and fill up the detection zone 26 with purge gas in a timely manner. Other related art laser modules have a plurality of purge holes that encircle the laser source 42. The purge hole pattern determines the fluid flow dynamics when the purge gas flows out of the detector housing 58b and into the detection zone 26. Generally the purge hole pattern encircling the laser source 42 requires a large volume of purge gas, and does not rapidly fill the volume outside the detector (i.e., the detection zone 26) with the purge gas, thereby slowing down the detection process.

In view of the above, a need has arisen to economically and rapidly purge gas from a detection zone during optical absorption spectroscopic measurement of gases in sealed containers.

SUMMARY OF THE DISCLOSURE

In order to accomplish gas detection a span of time shorter than using the aforementioned purge holes requires a more open apparatus that allows containers to enter and exit quickly. Additionally, ambient gas that is entrained with the parade of containers to be measured (not unlike a fan) can also be displaced by purge gas commensurately. A non-limiting feature of the disclosure rapidly and efficiently removes interfering gas species from a sample region. Another non-limiting feature of the disclosure improves the purge by introducing a more uniform flow of purge gas into the laser and detector path (i.e., the detection zone) via an annular ring or channel instead of the aforementioned discrete holes. The annular ring may be open all around the laser assembly and/or detector assembly, thereby providing a more uniform purge of the region of interest (such as a detection zone).

Another non-limiting feature of the disclosure requires less purge flow for the purposes of optical absorption spectroscopy than prior art designs, and displaces ambient gas in the inspection region more quickly. As a result of this improved purge, spurious signal from ambient gas can be eliminated and the measurement of the species of interest can be better qualified as being only from within a sealed container.

A feature of the disclosure provides a system for nondestructive detection of gas in a sealed container, the system having a light source housed in a light source housing and configured to emit a light beam for absorption in a substance to be measured, a detector housed in a detector housing and configured to detect the emitted light beam, a zone that accepts one or more of the sealed containers, each container being substantially optically transparent and containing the substance to be measured, the zone located between the detector and the light source, the light source configured to transmit the light beam through the zone, and a light source purging system having a light source channel surrounding the light source and positioned between the light source and the light source housing, the light source channel configured to expel purge gas from a purge gas source into the zone.

The light source channel may further be configured to expel the purge gas toward an optical axis of the light source. Additionally, the light source channel may completely and uninterruptingly surround the light source.

Also provided may be a lens housed in the detector housing and configured to focus the light beam onto the detector, the lens located between the zone and the detector, and a detector purging system having a detector channel surrounding the lens and positioned between the lens and the detector housing, the detector channel configured to expel purge gas into the zone the channel configured to expel purge gas into the zone.

The system may further include a lens frame configured to hold the lens, a plurality of lens frame channels positioned between the lens frame and the lens, each lens frame channel of the plurality of lens frame channels extending in the optical axis direction of the light source and configured to pass the purge gas from the purge gas source to the detector channel. Also, the thickness of the detector channel may be one millimeter or less in the optical axis direction of the light source.

Also, the detector channel may be further configured to expel the purge gas toward the optical axis of the light source. Further, the detector channel may completely and uninterruptingly surrounds the light source.

In another aspect, also provided may be a pre-purge system having at least one pre-purge aperture located in the light source housing on a side of the light source corresponding to an insertion direction of the container into the zone, the at least one purge aperture configured to pass the purge gas from the purge gas source into a region upstream of the zone. Additionally provided may be a pre-purge system having at least one pre-purge aperture located in the detector housing on a side of the detector corresponding to an insertion direction of the container into the zone, the at least one purge aperture configured to pass the purge gas from the purge gas source into a region upstream of the zone.

In another aspect, a system for detection of gas in a sealed container may be provided, the system having a light source housed in a light source housing and configured to emit a light beam for absorption in a substance to be measured, a detector housed in a detector housing and configured to detect the emitted light beam, a zone that accepts one or more of the sealed containers, each container being substantially optically transparent and containing the substance to be measured, the zone located between the detector and the light source, the light source configured to transmit the light beam through the zone, a lens housed in the detector housing and configured to focus the light beam onto the detector, the lens located between the zone and the detector, and a detector purging system having a detector channel surrounding the lens and positioned between the lens and the detector housing, the detector channel configured to expel purge gas into the zone the channel configured to expel purge gas from a purge gas source into the zone.

In a further aspect, a method for detection of gas in a sealed container may be provided, the method having providing a detection zone located between having a light source housed in a light source housing and configured to emit a light beam for absorption in a substance to be measured, and a detector housed in a detector housing and configured to detect the emitted light beam, the detection zone configured to accept one or more of the sealed containers, each container being substantially optically transparent and containing the substance to be measured, the light source configured to transmit the light beam through the zone onto the detector, expelling purge gas from a purge gas source into the detection zone via a light source channel surrounding the light source and positioned between the light source and the light source housing.

Also, the expelling may include expelling the purge gas toward an optical axis of the light source. Further, the light source channel may completely and uninterruptingly surrounds the light source.

Further, the expelling may include expelling the purge gas into the detection zone from the purge gas source via a detector channel surrounding a detector lens configured to focus the light beam onto the detector, the lens may be located between the detection zone and the detector, and the detector channel may be positioned between the detector lens and the detector housing.

Also, the expelling may further include passing the purge gas from the purge gas source to the detector channel through a plurality of lens frame channels positioned between a lens frame and the lens held by the lens frame, each lens frame channel of the plurality of lens frame channels extending in the optical axis direction of the light source.

In addition, the expelling may further include expelling the purge gas toward the optical axis of the light source. Also, in the method, the detector channel may completely and uninterruptingly surround the light source.

The method may further include pre-purgingly expelling the purge gas from the purge gas source into a region upstream of the detection zone prior to the expelling purge gas, via at least one purge aperture located in the light source housing on a side of the light source corresponding to an insertion direction of the container into the zone.

The method may additionally include pre-purgingly expelling the purge gas from the purge gas source into a region upstream of the detection zone prior to the expelling purge gas, via at least one purge aperture located in the detector housing on a side of the detector corresponding to an insertion direction of the container into the zone.

In a further aspect, a method for detection of gas in a sealed container may be provided, the method having providing a detection zone located between having a light source housed in a light source housing and configured to emit a light beam for absorption in a substance to be measured, and a detector housed in a detector housing and configured to detect the emitted light beam, the detection zone configured to accept one or more of the sealed containers, each container being substantially optically transparent and containing the substance to be measured, the light source configured to transmit the light beam through the zone onto the detector, expelling purge gas from a purge gas source into the detection zone via a detector channel surrounding the lens and positioned between the lens and the detector housing.

Other exemplary embodiments and advantages of the present invention may be ascertained by reviewing the present disclosure and the accompanying drawings, and the above description should not be considered to limit the scope of the present invention.

BRIEF DESCRIPTION OF THE DRAWINGS

The present invention is further described in the detailed description which follows, in reference to the noted plurality of drawings, by way of non-limiting examples of preferred embodiments of the present invention, in which like characters represent like elements throughout the several views of the drawings, and wherein.

DETAILED DESCRIPTION

In view of the foregoing, the present disclosure, through one or more of its various aspects, embodiments and/or specific features or sub-components, is thus intended to bring out one or more of the advantages as specifically noted below.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Referring now to the drawings wherein like characters represent like elements, FIGS. 4-7 show an optical absorption spectroscopy system 100 in accordance with a non-limiting aspect of the disclosure. The system 100 includes a light source 142 housed in a light source housing 158a, a light collection element 144 such as a lens, and a light detector 148. The light source 142 emits a light beam (e.g., a laser beam) through a substance to be measured in a sample container, the light collection element 144 and onto the light detector. The sample container is present in a detection zone 126 through which substantially transparent sample containers pass.

The light collection element 148 and light detector 148 are housed in a detector housing 158b. In alternative aspects, it is appreciated by those skilled in the art that the light detector 148 may include all elements needed to detect light emitted by the light source 148. It is also appreciated by those skilled in the art that while a laser light is described herein as the light source, the light source can be any suitable source of radiant energy. It is further noted that while a single light collection element 144 is shown on the side of the light detector, it is appreciated by those skilled in the art that a light collection element may be provided on the side of the light source alternatively or additionally to the light collection element on the side of the light detector, that that more than one light collection element may be implemented on either or both of the light detector side and the light source side.

Figure 4:
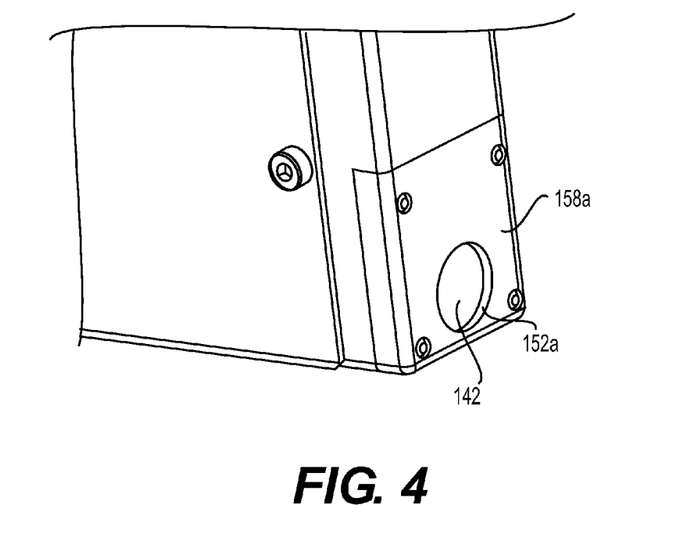
FIG. 4 shows a perspective view of a light source of the optical absorption laser spectroscopy system according to a non-limiting aspect of the present disclosure.
Figure 5:
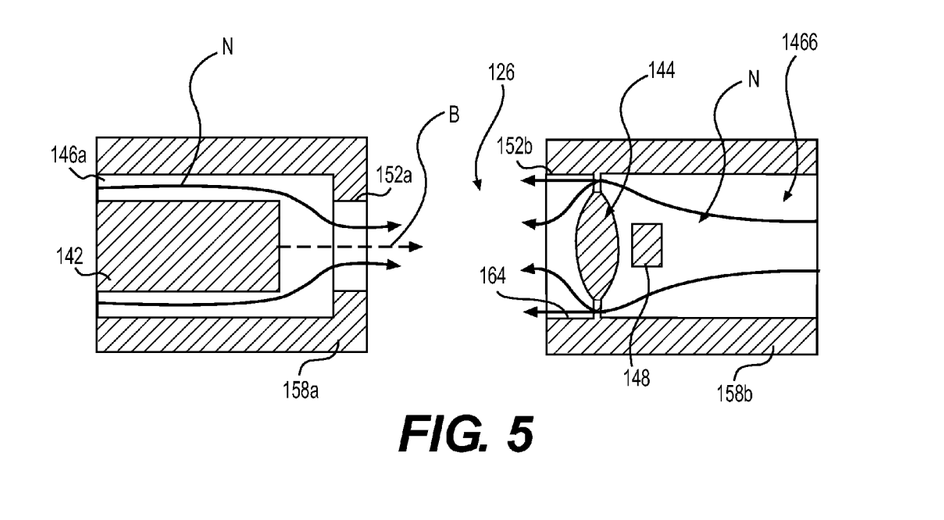
FIG. 5 shows a schematic side sectional optical absorption laser spectroscopy system according to a non-limiting aspect of the present disclosure

As shown in FIGS. 4-5, a light source purging system includes an annular light source channel 152a circumferentially surrounding the light source 142, which is in communication with a purge gas source via a supply pipe 146a. The annular channel 152a is located between the outside of the light source housing 158a facing the detection zone 126 and the light source 142. Rather than (or in addition to) providing discrete holes in the light source housing 158a, the annular channel 152a discharges purge gas such as nitrogen (or other inert gas that does not contain absorbers) toward an (optical) axis of light radiated from the light source 142 and then into the detection zone 126. The annular channel 152a improves the purge of the detection zone 126 by introducing a more uniform flow of purge gas into the detection zone, thereby providing a more uniform purge of the detection zone. Such a configuration allows purge gas to flow all around the light source and out into the detection zone 126.

Although the annular channel 152a is shown as being open around the entirety of the light source 142 (i.e., it is uninterrupted) it is appreciated by those skilled in the art that in alternative aspects, the annular channel may interrupted (i.e., the annular channel may include a plurality of arcuate channel segments arranged about the light source so that the light source is either completely or partially surrounded by the channels in a circumferential direction, each arcuate channel segment extending in an arc in the circumferential direction). In one aspect, the thickness of the annular channel 152a is one millimeter or less in the optical axis direction of the lens.

Figure 6:
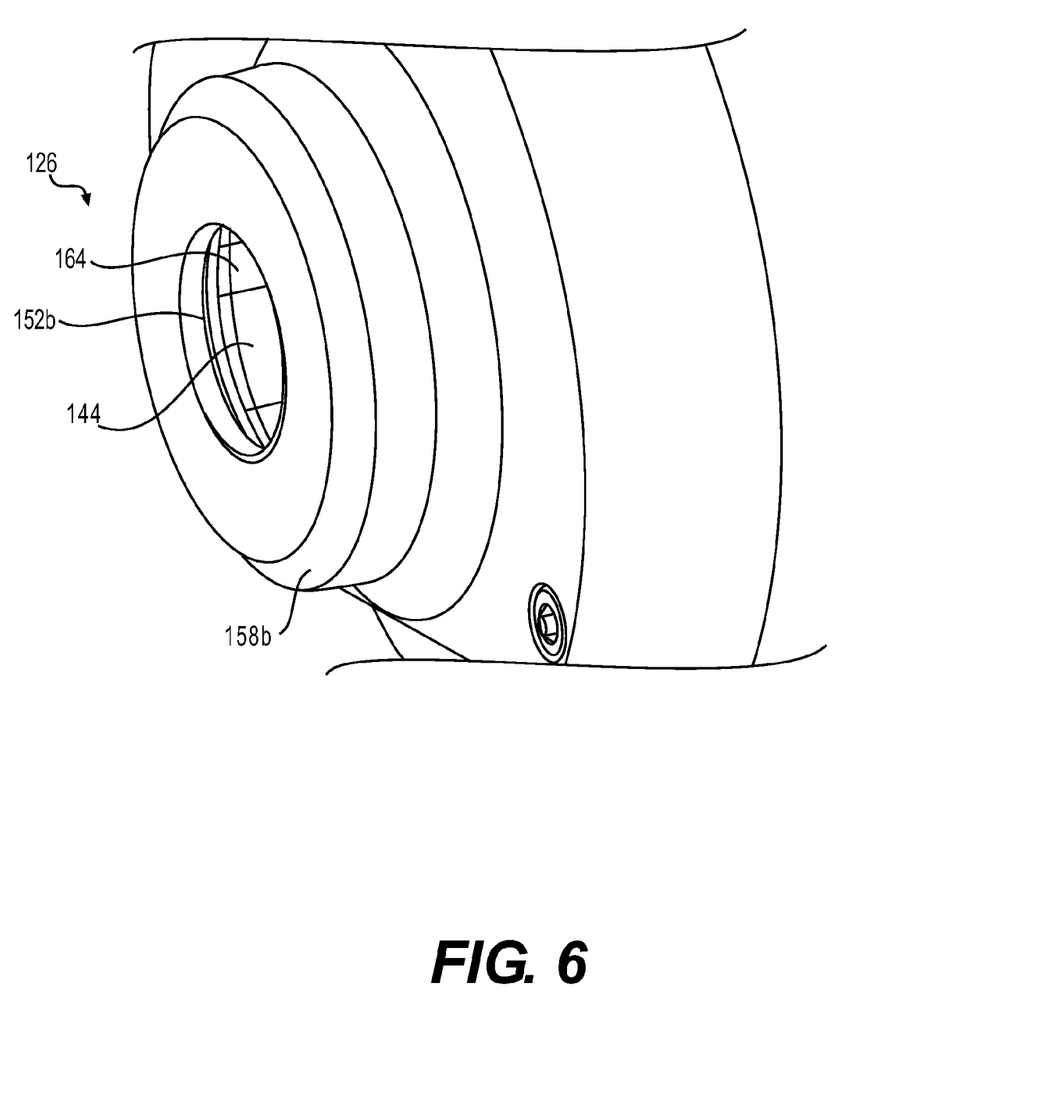
FIG. 6 shows a perspective view of a detector of the optical absorption laser spectroscopy system according to a non-limiting aspect of the present disclosure.
Figure 7:
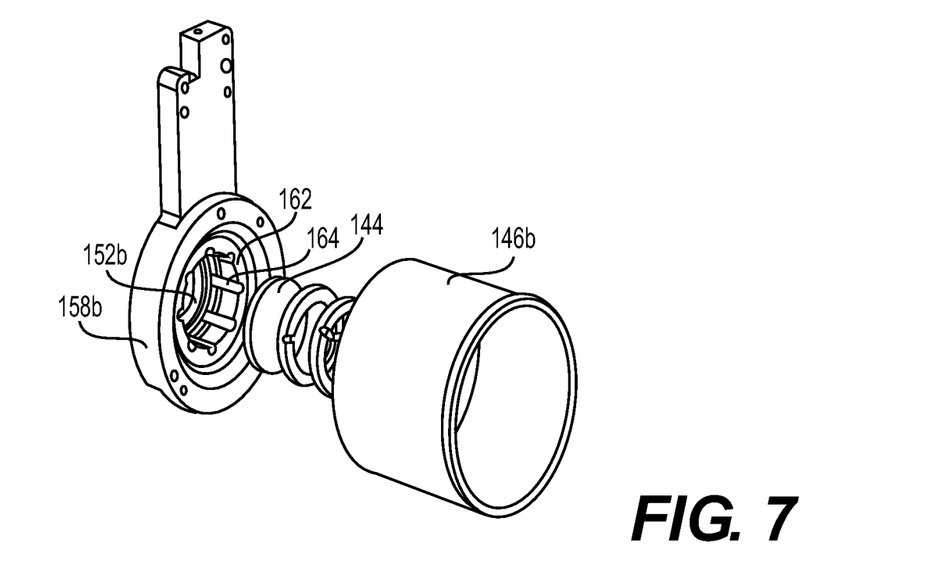
FIG. 7 shows an exploded view of the detector of the optical absorption laser spectroscopy system according to a non-limiting aspect of the present disclosure.

As shown in FIGS. 5-7, a detector purging system includes an annular detector channel 152b circumferentially surrounding the lens 144, which is in communication with a purge gas source via a supply pipe 146b. The annular channel 152b is located between the outside of the detector housing 158b facing detection zone 126 and the lens 144. Rather than (or in addition to) providing discrete holes in the detector housing 158b, the annular channel 152b discharges the purge gas toward the optical axis of lens 144 and then into the detection zone 126. As with the light source channel 152a, the detector channel 152b improves the purge of the detection zone 126 by introducing a more uniform flow of purge gas into the detection zone, thereby providing a more uniform purge of the detection zone. Thus configuration allows purge gas to flow all around the lens 144 and out into the detection zone 126.

Although the annular channel 152b is shown as being open around the entirety of the lens 144 (i.e., it is uninterrupted) it is appreciated by those skilled in the art that in alternative aspects, the annular channel may interrupted (i.e., the annular channel may include a plurality of arcuate channel segments arranged about the lens so that the lens is either completely or partially surrounded by the channels in a circumferential direction, each arcuate channel segment extending in an arc in the circumferential direction).

As shown in FIG. 7, the detector purging system also includes a lens frame 162 which holds the lens 144. The lens frame includes one or more axial lens frame channels 164, each lens frame channel generally extending in a direction N of purge gas flow from the supply pipe 146b (which is also a direction generally parallel to the optical axis of the lens 144, and which is further a direction orthogonal to a plane passing through the entire annular channel 152b). Further, each lens frame is in open communication on one end thereof with the supply pipe 146b and on the other end thereof with the annular channel 152b, so that purge gas passes from the supply pipe 146b, through the axial frame channels 164, into the annular channel(s) 152b and then into the detection zone 126. In one aspect, the annular channel 152b is defined in the optical axis direction by the lens 144 on one side, and the inside of the detector housing 158b on the other side and the thickness of the annular channel 152b may be one millimeter or less in the optical axis direction of the lens.

Although the figures show eight axial frame channels 164 equally spaced about the lens 144, those skilled in the art would appreciate that more or less than eight axial frame channels may be employed, and that the spacing between the axial frame channels need not be equally spaced. It is noted that the light source purging system and detector purging system are collectively referred to as the spectroscopy system purging system, and that while the optical absorption spectroscopy system 100 includes both the light source purging system and detector purging system each of which expels purging gas on an opposite side of the detection zone 126, in alternative aspects, only a light source purging system or only a detector purging system may be provided.

Figure 8:
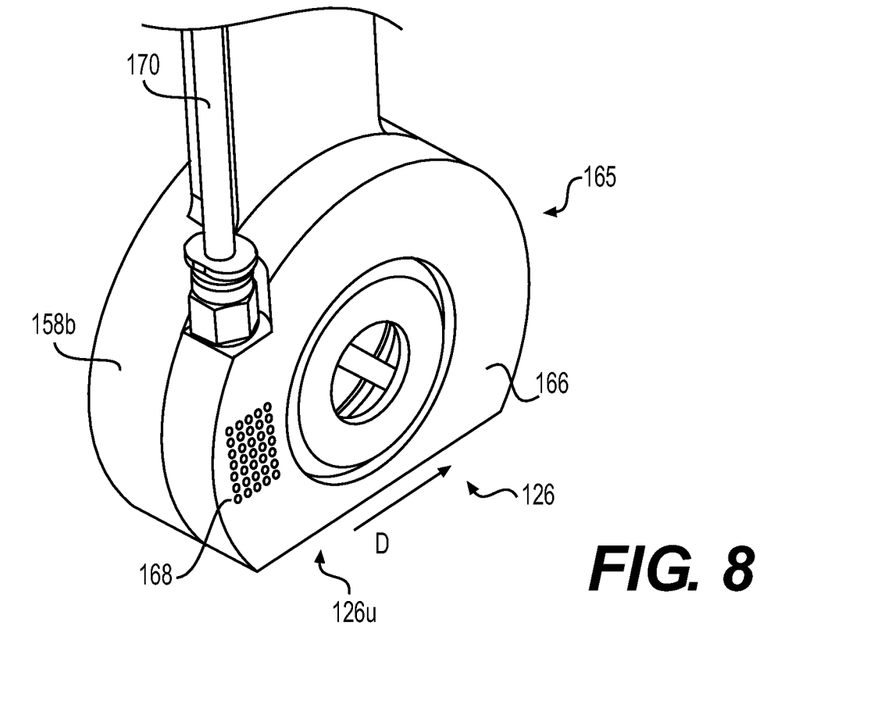
FIG. 8 shows a perspective view of a pre-purge system of the optical absorption laser spectroscopy system according to a non-limiting aspect of the present disclosure.

FIG. 8 shows a further feature of the optical absorption spectroscopy system 100 which includes a pre-purging system 165 configured to expel purge gas from a plurality of pre-purge apertures 168. Specifically, the purge gas may be supplied from gas purge line 170 into a pre-purge cap 166 installed over the detector housing 158b surrounding the lens 144 (so as not to interfere with the purge gas being expelled from the annular channel 152b). The pre-purge apertures 168 are configured to expel purge gas into a region upstream 126u (in relation to a direction of flow D of sample container) of the detection zone 126. In the case of rapid movement of the sample containers into the detection zone 126, the pre-purging system 165 expands the area to be purged beyond the detection zone 126, i.e., to the area 126u before the sample container enters the detection zone, which reduces the amount of ambient air that the light source purging system and/or detector purging system has to displace. Thus, depending on the specific configuration of the sample containers and the means by which the sample containers are passed through the detection zone 126, the purge gas exiting from the system 100 may be directed wholly or partially in the direction of the sample containers incoming to the detection zone in order to counteract the effects of the ambient gas entrainment. Although FIG. 8 shows the pre-purging system 168 used in conjunction with the detector side of the system 100, it is appreciated by those of skill in the art that the pre-purging system may additionally or alternatively used in conjunction with the light source side of the system.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Unless otherwise indicated, all numbers expressing quantities of ingredients and the like used in the specification and claims are to be understood as being modified in all instances by the term "about." The terms "generally" and "approximately" as used herein are to be understood as an approximation allowing for variations while still maintaining the efficacy of the invention. Accordingly, unless indicated to the contrary, the numerical and geometric parameters and relationships set forth in the following specification and attached claims are approximations that may vary depending upon the desired properties sought to be obtained by the present invention. At the very least, and not as an attempt to limit the application of the doctrine of equivalents to the scope of the claims, each numerical and geometric parameters and relationship should be construed in light of the number of significant digits and ordinary rounding approaches.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system for nondestructive detection of gas in a sealed container, the system comprising:
    a light source housed inside a light source housing and configured to emit a light beam for absorption in a substance to be measured;
    a detector housed in a detector housing and configured to detect the emitted light beam;

a zone that accepts one or more of the sealed containers, each container being substantially optically transparent and containing the substance to be measured, the zone located between the detector and the light source, the light source configured to transmit the light beam through the zone; and a light source purging system comprising a light source purge gas channel surrounding the light source and positioned between the light source and the light source housing, the light source purge gas channel configured to expel purge gas from a purge gas source into the zone.

2. The system according to claim 1, wherein the light source purge gas channel is further configured to expel the purge gas toward an optical axis of the light source.

3. The system according to claim 1, wherein the light source purge gas channel completely and uninterruptingly surrounds the light source.

4. The system according to claim 1, further comprising:
a lens housed in the detector housing and configured to focus the light beam onto the detector, the lens located between the zone and the detector; and
a detector purging system comprising a detector purge gas channel surrounding the lens and positioned between the lens and the detector housing, the detector purge gas channel configured to expel purge gas into the zone.

5. The system according to claim 4, further comprising:
a lens frame configured to hold the lens;
a plurality of lens frame channels positioned between the lens frame and the lens, each lens frame channel of the plurality of lens frame channels extending in the optical axis direction of the light source and configured to pass the purge gas from the purge gas source to the detector purge gas channel.

6. The system according to claim 4, wherein a thickness of the detector purge gas channel is one millimeter or less in the optical axis direction of the light source.

7. The system according to claim 4, wherein the detector purge gas channel is further configured to expel the purge gas toward the optical axis of the light source.

8. The system according to claim 4, wherein the detector purge gas channel completely and uninterruptingly surrounds the light source.

9. The system according to claim 1, further comprising a pre-purge system comprising at least one pre-purge aperture located in the light source housing on a side of the light source corresponding to an insertion direction of the container into the zone, the at least one purge aperture configured to pass the purge gas from the purge gas source into a region upstream of the zone.

10. The system according to claim 1, further comprising a pre-purge system comprising at least one pre-purge aperture located in the detector housing on a side of the detector corresponding to an insertion direction of the container into the zone, the at least one purge aperture configured to pass the purge gas from the purge gas source into a region upstream of the zone.

11. A system for detection of gas in a sealed container, the system comprising:
a light source housed inside a light source housing and configured to emit a light beam for absorption in a substance to be measured;
a detector housed in a detector housing and configured to detect the emitted light beam;
a zone that accepts one or more of the sealed containers, each container being substantially optically transparent and containing the substance to be measured, the zone located between the detector and the light source, the light source configured to transmit the light beam through the zone;
a lens housed completely inside the detector housing and configured to focus the light beam onto the detector, the lens located between the zone and the detector; and
a detector purging system comprising a detector purge gas channel surrounding the lens and positioned between the lens and the detector housing, the detector purge gas channel configured to expel purge gas from a purge gas source into the zone.

12. A method for detection of gas in a sealed container, the method comprising:
in a detection zone located between a light source housed inside a light source housing and configured to emit a light beam for absorption in a substance to be measured, and a detector housed in a detector housing and configured to detect the emitted light beam, the detection zone configured to accept one or more of the sealed containers, each container being substantially optically transparent and containing the substance to be measured, the light source configured to transmit the light beam through the zone onto the detector, expelling purge gas from a purge gas source into the detection zone via a light source purge gas channel surrounding the light source and positioned between the light source and the light source housing.

13. The method according to claim 12, wherein said expelling comprises expelling the purge gas toward an optical axis of the light source.

14. The method according to claim 12, wherein the light source purge gas channel completely and uninterruptingly surrounds the light source.

15. The method according to claim 12, wherein:
said expelling comprises expelling the purge gas into the detection zone from the purge gas source via a detector purge gas channel surrounding a detector lens configured to focus the light beam onto the detector;
the lens is located between the detection zone and the detector; and
the detector purge gas channel is positioned between the detector lens and the detector housing.

16. The method according to claim 15, wherein said expelling further comprises passing the purge gas from the purge gas source to the detector purge gas channel through a plurality of lens frame channels positioned between a lens frame and the lens held by the lens frame, each lens frame channel of the plurality of lens frame channels extending in the optical axis direction of the light source.

17. The method according to claim 15, wherein said expelling further comprises expelling the purge gas toward the optical axis of the light source.

18. The method according to claim 15, wherein the detector purge gas channel completely and uninterruptingly surrounds the light source.

19. The method according to claim 12, further comprising pre-purgingly expelling the purge gas from the purge gas source into a region upstream of the detection zone prior to said expelling purge gas, via at least one purge aperture located in the light source housing on a side of the light source corresponding to an insertion direction of the container into the zone.

20. The method according to claim 12, further comprising pre-purgingly expelling the purge gas from the purge gas source into a region upstream of the detection zone prior to said expelling purge gas, via at least one purge aperture located in the detector housing on a side of the detector corresponding to an insertion direction of the container into the zone.

21. A method for detection of gas in a sealed container, the method comprising:

in a detection zone located between a light source housed inside a light source housing and configured to emit a light beam for absorption in a substance to be measured, and a detector housed in a detector housing and configured to detect the emitted light beam and a lens housed completely inside the detector housing and focusing the light beam onto the detector, the lens positioned between the zone and the detector, the detection zone configured to accept one or more of the sealed containers, each container being substantially optically transparent and containing the substance to be measured, the light source configured to transmit the light beam through the zone onto the detector expelling purge gas from a purge gas source into the detection zone via a detector purge gas channel surrounding the lens and positioned between the lens and the detector housing.

22. The system according to claim 1, wherein the light source is recessed inside the light source housing in an optical axis direction of the light beam.

23. The system according to claim 11, wherein the detector is recessed inside the detector housing in an optical axis direction of the light beam.

24. The system according to claim 1, wherein the light source purge gas channel is a single channel coaxial to an optical axis of the light beam.

25. The system according to claim 11, wherein the detector purge gas channel is a single channel coaxial to an optical axis of the light beam.

26. A system for nondestructive detection of gas in a sealed container, the system comprising:

a light source housed inside a light source housing and configured to emit a light beam for absorption in a substance to be measured;

a detector housed in a detector housing and configured to detect the emitted light beam;

a zone that accepts one or more of the sealed containers, each container being substantially optically transparent and containing the substance to be measured, the zone located between the detector and the light source, the light source configured to transmit the light beam through the zone;

lens housed in the detector housing and configured to focus the light beam onto the detector, the lens located between the zone and the detector; and a purging system comprising:

a light source purge gas channel surrounding the light source and positioned between the light source and the light source housing, the light source purge gas channel configured to expel purge gas from a purge gas source into the zone; and a detector purge gas channel surrounding the lens and positioned between the lens and the detector housing, the detector purge gas channel configured to expel the purge gas from the purge gas source into the zone.

\* \* \* \* \*

UNITED STATES PATENT AND TRADEMARK OFFICE
CERTIFICATE OF CORRECTION

PATENT NO. : 9,176,050 B2
APPLICATION NO. : 13/839774
DATED : November 3, 2015
INVENTOR(S) : W. Griffith et al.

It is certified that error appears in the above-identified patent and that said Letters Patent is hereby corrected as shown below:

Claims
Column 11, line 18 (claim 21, line 15) "detector expelling" should be -- detector, expelling --.

Signed and Sealed this
Fourteenth Day of June, 2016

Michelle K. Lee
*Director of the United States Patent and Trademark Office*